US00PP19170P2

(12) United States Plant Patent
Brown

(10) Patent No.: US PP19,170 P2
(45) Date of Patent: Sep. 2, 2008

(54) ***ARCTOTIS* PLANT NAMED 'ARC406'**

(50) Latin Name: *Arctotis hybrida*
Varietal Denomination: ARC406

(75) Inventor: Graham Noel Brown, Pennant Hills (AU)

(73) Assignee: Amerinova Properties LLC, Bonsall, CA (US)

( * ) Notice: Subject to any disclaimer, the term of this patent is extended or adjusted under 35 U.S.C. 154(b) by 0 days.

(21) Appl. No.: 11/800,775

(22) Filed: May 7, 2007

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner*—Annette H Para
(74) *Attorney, Agent, or Firm*—C. A. Whealy

(57) ABSTRACT

A new and distinct cultivar of *Arctotis* plant named 'ARC406', characterized by its compact, upright and mounded plant habit; freely branching growth habit; relatively small leaves; single-type inflorescences with golden yellow-colored ray florets and disc florets that are nearly black in color; and good garden performance.

1 Drawing Sheet

Botanical designation: *Arctotis hybrida.*
Cultivar denomination: 'ARC406'.

BACKGROUND OF THE INVENTION

The present invention relates to a new and distinct cultivar of *Arctotis* plant, botanically known as *Arctotis hybrida* and hereinafter referred to by the name 'ARC406'.

The new *Arctotis* is a product of a planned breeding program conducted by the Inventor in Cobbitty, New South Wales, Australia. The objective of the breeding program is to create new compact *Arctotis* cultivars that tolerate high temperatures.

The new *Arctotis* originated from a self-pollination in October, 2001 in Cobbitty, New South Wales, Australia of a proprietary selection of *Arctotis hybrida* identified as code number 2000.15, not patented. The new *Arctotis* was discovered and selected by the Inventor as a single flowering plant within the progeny of the stated self-pollination in a controlled environment in Cobbitty, New South Wales, Australia in October, 2002.

Asexual reproduction of the new *Arctotis* by vegetative tip cuttings in a controlled environment in Cobbitty, New South Wales, Australia since October, 2002 has shown that the unique features of this new *Arctotis* are stable and reproduced true to type in successive generations.

SUMMARY OF THE INVENTION

Plants of the cultivar ARC406 have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'ARC406'. These characteristics in combination distinguish 'ARC406' as a new and distinct potted *Arctotis* cultivar:

1. Compact, upright and mounded plant habit.
2. Freely branching growth habit.
3. Relatively small leaves.

4. Single-type inflorescences with golden yellow-colored ray florets and disc florets that are nearly black in color.
5. Good garden performance.

Plants of the new *Arctotis* differ from plants of the parent selection in the following characteristics:

1. Plants of the new *Arctotis* have smaller leaves than plants of the parent selection.
2. Plants of the new *Arctotis* have smaller inflorescences than plants of the parent selection.
3. Plants of the new *Arctotis* and the parent selection differ in ray floret color as plants of the parent selection have yellow orange-colored ray florets.

Plants of the new *Arctotis* can be compared to plants of the *Arctotis* cultivar Archley, disclosed in U.S. Plant Pat. No. 14,667. In side-by-side comparisons conducted in Cobbitty, New South Wales, Australia, plants of the new *Arctotis* differed from plants of the cultivar Archley in the following characteristics:

1. Plants of the new *Arctotis* were more mounding than plants of the cultivar Archley.
2. Plants of the new *Arctotis* had smaller leaves than plants of the cultivar Archley.
3. Plants of the new *Arctotis* had smaller inflorescences than plants of the cultivar Archley.
4. Plants of the new *Arctotis* and the cultivar Archley differed in ray floret color as plants of the cultivar Archley had yellow orange-colored ray florets.

BRIEF DESCRIPTION OF THE PHOTOGRAPHS

The accompanying photographs illustrate the overall appearance of the new *Arctotis.* These photographs show the colors as true as it is reasonably possible to obtain in colored reproductions of this type. Colors in the photographs may differ slightly from the color values cited in the detailed botanical description which accurately describe the colors of the new *Arctotis.*

The photograph at the bottom of the sheet comprises a side perspective view of a typical flowering plant of 'ARC406'.

The photograph at the top of the sheet is a close-up view of a typical inflorescence of 'ARC406'.

DETAILED BOTANICAL DESCRIPTION

The aforementioned photographs and following observations and measurements describe plants grown in an outdoor nursery during the autumn and winter in Bonsall, Calif. and under conditions and practices which approximate those generally used in commercial potted *Arctotis* production. During the production of the plants, day temperatures ranged from about 16° C. to about 27° C. and night temperatures ranged from about 10° C. to 21° C. Plants were pinched one time. Plants used in the photographs and for the description were about nine weeks old. In the following description, color references are made to The Royal Horticultural Society Colour Chart, 1995 Edition, except where general terms of ordinary dictionary significance are used.

Botanical classification: *Arctotis hybrida* cultivar ARC406.

Parentage: Self-pollination of a proprietary selection of *Arctotis hybrida* identified as code number 2000.15, not patented.

Propagation:

*Type.*—Terminal cuttings.

*Time to initiate roots, summer.*—About twelve days at temperatures of 28° C. to 35° C.

*Time to produce a rooted young plants, summer.*—About four weeks at temperatures of 28° C. to 35° C.

*Time to produce a rooted young plants, winter.*—About five weeks at temperatures of 20° C. to 25° C.

*Root description.*—Fibrous; white in color.

*Rooting habit.*—Freely branching; dense.

Plant description:

*Appearance.*—Herbaceous single-type potted *Arctotis*. Compact, upright and mounded plant habit. Freely branching growth habit with about eight lateral branches. Vigorous growth habit.

*Plant height, to top of foliar plane.*—About 16 cm.

*Plant height, to top of inflorescences.*—About 27 cm.

*Plant width.*—About 30 cm.

*Lateral branches.*—Length: About 13 cm. Diameter: About 4.5 mm. Internode length: About 5 mm. Strength: Strong. Texture: Pubescent. Color: 194C.

Foliage description:

*Arrangement.*—Alternate, simple.

*Length.*—About 3.7 cm.

*Width.*—About 2.1 cm.

*Shape.*—Spatulate.

*Apex.*—Broadly acute to rounded.

*Base.*—Attenuate.

*Margin.*—Irregularly serrated.

*Texture, upper and lower surfaces.*—Pubescent.

*Venation pattern.*—Pinnate, arcuate.

*Color.*—Developing foliage, upper surface: 191A to 191B. Developing foliage, lower surface: 198B. Fully expanded foliage, upper surface: 147A; venation, 191B. Fully expanded foliage, lower surface: 191A: venation, 191C.

*Petiole length.*—About 3.8 cm.

*Petiole diameter.*—About 3 mm.

*Petiole texture, upper and lower surfaces.*—Pubescent.

*Petiole color, upper surface.*—147C.

*Petiole color, lower surface.*—148B to 148C.

Inflorescence description:

*Appearance.*—Single-type inflorescence form with ligulate-shaped ray florets. Inflorescences borne on terminal and axillary peduncles above foliage. Disk and ray florets arranged acropetally on a capitulum. Inflorescences not fragrant.

*Flowering season.*—Plants flower from October to June in Southern California; flowering continuous during this period.

*Inflorescence longevity.*—Inflorescences last about three to four days on the plant; inflorescences persistent.

*Quantity of inflorescences.*—Freely flowering, about 20 inflorescences develop per plant.

*Inflorescence bud.*—Height: About 2.8 cm. Diameter: About 1.1 cm. Shape: Rounded to ovate. Color: 166C to 166D.

*Inflorescence size.*—Diameter: About 7 cm. Depth (height): About 2.5 cm to 3 cm. Diameter of disc: About 1.4 cm. Receptacle height: About 1 cm. Receptacle diameter: About 1.1 cm.

*Ray florets.*—Shape: Ligulate. Orientation: Initially upright, then perpendicular to the peduncle; apices reflexed. Length: About 3.6 cm. Width: About 6 mm. Apex: Acute. Base: Acute. Margin: Entire. Texture, upper and lower surfaces: Smooth, glabrous; velvety. Number of ray florets per inflorescence: About 18 arranged in a single whorl. Color: When opening, upper surface: 13B. When opening, lower surface: 166D. Fully opened, upper surface: 13A; towards the base, 166A. Fully opened, lower surface: 12C; longitudinal stripes, 172A to 172B.

*Disc florets.*—Arrangement: Massed at center of receptacle. Shape: Tubular, elongated. Apex: Five-pointed. Length: About 8 mm. Width, at apex: About 1.5 mm. Width, at base: About 1 mm. Number of disc florets per inflorescence: About 98. Color, immature: Apex: Close to 202A. Mid-section: 177A. Base: 155D. Color, mature: Apex: 199A. Mid-section: 199B. Base: 155D.

*Phyllaries.*—Number of phyllaries per inflorescence: About 24 in four whorls. Length: About 9 mm to 11 mm. Width: About 4 mm. Shape: Elliptic. Apex: Acute. Base: Truncate. Margin: Entire. Texture, upper surface: Smooth, glabrous. Texture, lower surface: Pubescent. Color, upper surface: 146C. Color, lower surface: 148B.

*Peduncles.*—Length: About 16.8 cm. Diameter: About 2 mm. Angle: Mostly erect. Strength: Strong, flexible. Texture: Pubescent. Color: 148C.

*Reproductive organs.*—Androecium: Quantity per disc floret: Five. Filament length: About 1.5 mm. Filament color: Close to 157D. Anther shape: Lanceolate. Anther length: About 2 mm. Anther color: Close to 79A. Pollen amount: Scarce. Pollen color: Close to 21A. Gynoecium: Pistil length: About 7 mm. Stigma shape: Two-parted. Stigma color: 199A. Style length: About 4 mm. Style color: 153D. Ovary color: 157A.

*Seed/fruit.*—Seed and fruit production has not been observed.

Disease/pest resistance: Resistance to pathogens and pests common to *Arctotis* has not been observed on plants grown under commercial conditions.

Garden performance: Plants of the new *Arctotis* have been observed to have good garden performance and to tolerate wind, rain and temperatures from about 5° C. to about 40° C.

It is claimed:

1. A new and distinct *Arctotis* plant named 'ARC406' as illustrated and described.

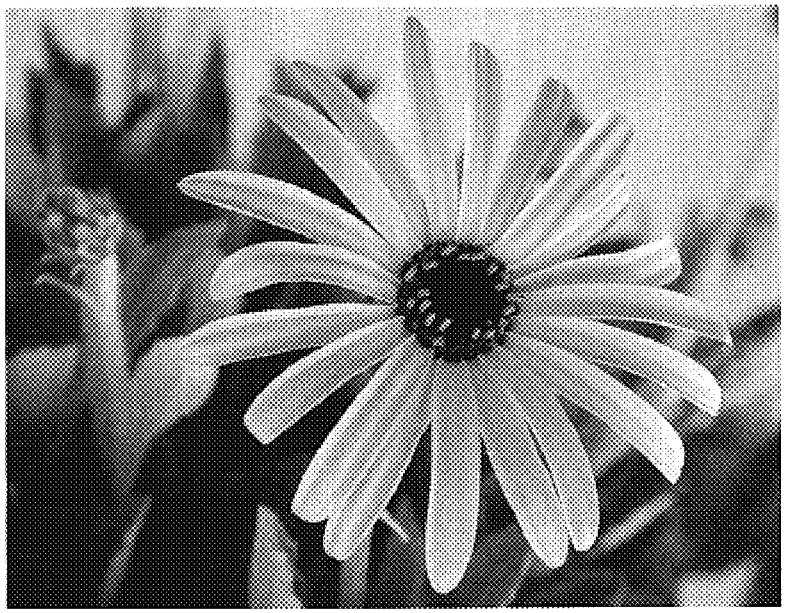
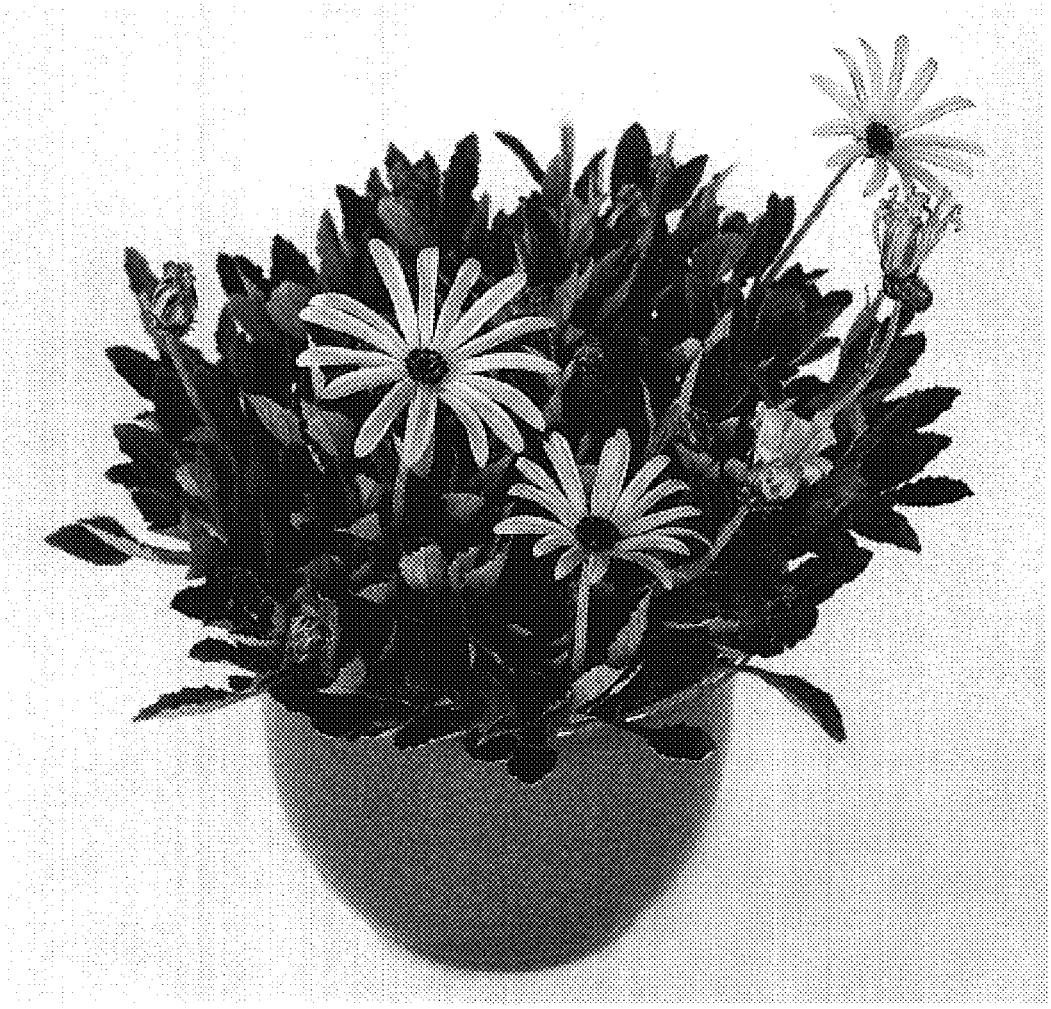

* * * * *